(12) United States Patent
Magalich et al.

(10) Patent No.: US 8,657,795 B2
(45) Date of Patent: Feb. 25, 2014

(54) VASCULAR PORT

(75) Inventors: Christopher N. Magalich, Apollo, PA (US); Scott K. Philhower, Bloomington, IN (US); Shawn Nichols, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 674 days.

(21) Appl. No.: 12/649,696

(22) Filed: Dec. 30, 2009

(65) Prior Publication Data

US 2011/0160673 A1 Jun. 30, 2011

(51) Int. Cl.
*A61M 37/00* (2006.01)

(52) U.S. Cl.
USPC .................................. 604/288.02

(58) Field of Classification Search
USPC ............... 604/174, 175, 178, 288.01–288.04, 604/533–536, 539
See application file for complete search history.

(56) References Cited

U.S. PATENT DOCUMENTS

| | | | |
|---|---|---|---|
| 4,673,394 A | 6/1987 | Fenton et al. | |
| 4,723,948 A | 2/1988 | Clark et al. | |
| 5,044,955 A | 9/1991 | Jagmin | |
| 5,201,715 A | 4/1993 | Masters | |
| 5,722,959 A * | 3/1998 | Bierman | 604/174 |
| 6,287,293 B1 | 9/2001 | Jones et al. | |
| 6,290,677 B1 | 9/2001 | Arai et al. | |
| 6,527,754 B1 | 3/2003 | Tallarida et al. | |
| 6,572,590 B1 | 6/2003 | Stevens et al. | |
| 7,087,038 B2 | 8/2006 | Lee | |
| 7,387,624 B2 | 6/2008 | Nelson | |
| 7,452,354 B2 | 11/2008 | Bright et al. | |
| 2004/0002693 A1* | 1/2004 | Bright et al. | 604/533 |
| 2005/0192559 A1 | 9/2005 | Michels et al. | |
| 2006/0064159 A1 | 3/2006 | Porter et al. | |
| 2006/0224129 A1 | 10/2006 | Beasley et al. | |
| 2006/0247584 A1 | 11/2006 | Sheetz et al. | |
| 2006/0264814 A1* | 11/2006 | Sage | 604/67 |
| 2007/0123831 A1 | 5/2007 | Haindl et al. | |
| 2007/0233017 A1 | 10/2007 | Zinn et al. | |
| 2008/0140025 A1 | 6/2008 | Sheetz et al. | |
| 2008/0183154 A1 | 7/2008 | Racz et al. | |
| 2008/0319421 A1* | 12/2008 | Bizup et al. | 604/535 |
| 2009/0024098 A1 | 1/2009 | Bizup et al. | |
| 2009/0112187 A1 | 4/2009 | Goode et al. | |
| 2009/0118683 A1 | 5/2009 | Hanson et al. | |
| 2009/0156928 A1 | 6/2009 | Evans et al. | |
| 2009/0204072 A1 | 8/2009 | Amin et al. | |
| 2009/0227862 A1 | 9/2009 | Smith et al. | |
| 2010/0069743 A1 | 3/2010 | Sheetz et al. | |

OTHER PUBLICATIONS

"IsoMed Constant-Flow Infusion System Fact Sheet". Medtronic. <http://wwwp.medtronic.com/Newsroom/LinkedItemDetails.do?itemId=1101853461258&itemType=fact_sheet&lang=en_US>. Accessed via the Internet Archive WayBack Machine, as it appeared on Mar. 22, 2006.*
Excela Product Brochure.

* cited by examiner

*Primary Examiner* — Kami A Bosworth
(74) *Attorney, Agent, or Firm* — Woodard, Emhardt, Moriarty, McNett & Henry LLP

(57) ABSTRACT

An access port for subcutaneous use in a patient is disclosed. This may include one or more of a housing; a chamber; a needle-penetrable sealing septum providing needle access to said chamber; and a male projection having therein a conduit to said chamber, with the projection adapted to receive a catheter. It may also include one or more of a lock and/or a locking button movable with respect to said housing. Such movement may be transverse and/or may include a yoke or other member applying inward force on the catheter.

18 Claims, 11 Drawing Sheets

US 8,657,795 B2

VASCULAR PORT

BACKGROUND

The present invention relates to vascular ports, and more specifically to subcutaneous vascular ports having a lock to hold a catheter onto the port.

Vascular ports, such as subcutaneous vascular ports, are used in the medical field. They typically include housing with a chamber in the housing and a needle-penetrable sealing septum that provides needle access to the chamber. Such needle access typically is made percutaneously, through the septum to provide for repeated needle access, such as for injecting fluids and/or withdrawing fluids from the patient via the port.

Such ports typically have a male projection over which the catheter is received. A variety of locking mechanisms have been used that have various advantages and disadvantages with their designs.

Also, such ports may include or not include radio-opaque marking, such as marking indicating rated flow rate or other attributes of the port.

Also, such access ports may have more than one chamber and/or more than one sealing septum and/or more than one catheter connected thereto.

Thus, there is a need for improvement in this field.

SUMMARY

The present inventions are defined by the claims, and only the claims. As set forth in the claims, such inventions may include the optional elements of an access port for subcutaneous use in a patient. This may include one or more of a housing; a chamber; a needle-penetrable sealing septum providing needle access to said chamber; and a male projection having therein a conduit to said chamber, with the projection adapted to receive a catheter. It may also include one or more of a lock and/or a locking button movable with respect to said housing. Such movement may be transverse and/or may include a yoke or other member applying inward force on the catheter.

Further forms, objects, features, aspects, benefits, advantages, and embodiments of the present invention will become apparent from a detailed description and drawings provided herewith.

DESCRIPTION OF THE SELECTED EMBODIMENTS

Figure 1A:
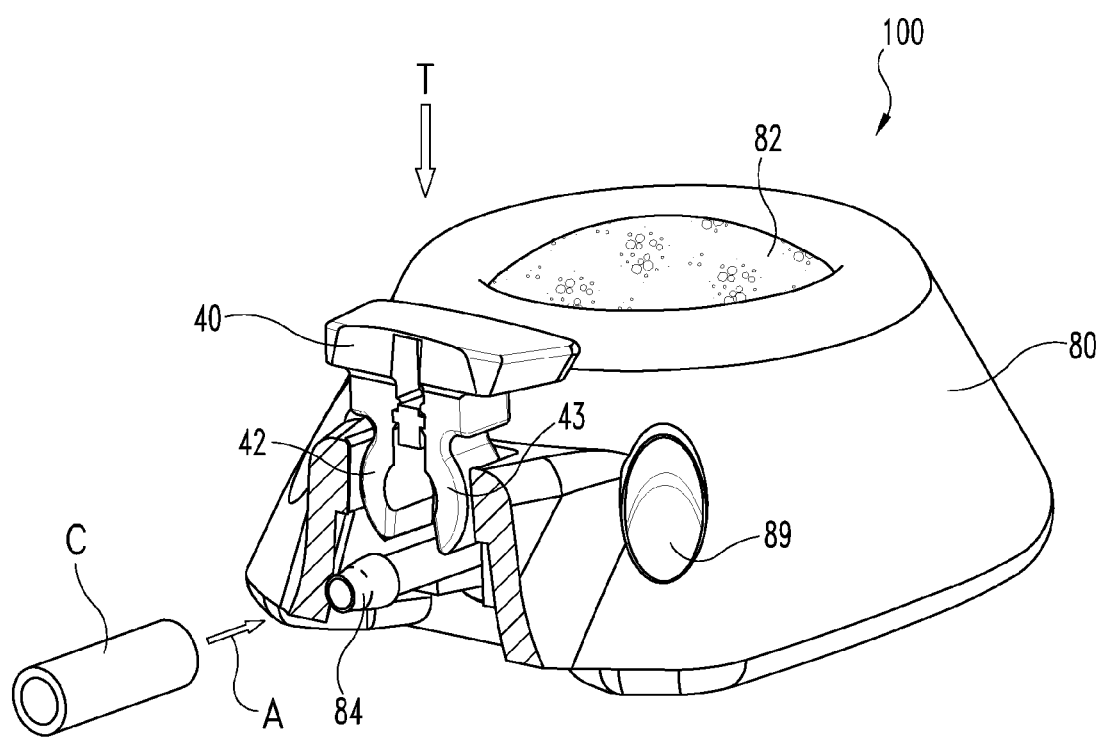
FIG. 1A is a perspective view of one example of a device according to the present invention(s) about to receive a catheter.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. One embodiment of the invention is shown in great detail, although it will be apparent to those skilled in the relevant art that some features that are not relevant to the present invention may not be shown for the sake of clarity.

As used in the claims and the specification, the following terms have the following definitions:

The term "access port" means a port that provides repeated access to a medical patient's blood vessels or other body vessels or cavities for purposes of adding and/or withdrawing fluids.

The term "attached" means mechanically connected, even if movable, such that it will not fall loose from that which it is mechanically connected. This may be accomplished by, without limitation, tracks, detents, integral components, living hinges, pivot mounts, and/or otherwise, and/or a combination thereof.

The term "catheter" means flexible medical tubing. It may include or not include radio-opaque marking. It may include or not include reinforcement; it may include or not include other structures or features attached to it. It may have one, two or more lumens.

The term "chamber" means a three-dimensional space.

The term "conduit" means a lumen or passageway through a structure sufficiently large to allow the passage of fluids.

The term "detent" means a structural interface including one or more projections and associated recesses to help hold, or at least resist against movement, from one position to another position.

The term "elastically deform" means deformation which is not plastic or permanent.

The term "generally transverse" means an orientation with respect to an axial direction, such as the axis of a catheter or conduit, which is greater than negative forty-five degrees (−45°) or less than forty-five degrees (45°) from perpendicular/normal to such axis.

The term "housing" means a structure which directly or indirectly defines, surrounds and/or supports one or more chambers therein.

The term "integral" means made from the same piece of material, such as for example, commonly molded in the same piece of plastic and/or commonly machined in the same piece of metal.

The term "inward" means generally radially inward with respect to the lumen of the catheter and/or a conduit.

The term "lock" means a mechanical structure which helps hold something else in place. A lock may be a single piece, or multiple pieces in contact with each other and/or separate from each other but working in cooperation.

The term "locked position" means a spatial relationship wherein a lock helps hold something else in place.

The term "male projection" means a structure that extends and may be inserted into something else.

The term "member" means a solid structure made of one or more pieces. It may be rigid, flexible, or both.

The term "movable" means adapted to have its position changed.

The term "needle access" means adapted to receive a medical needle to add and/or withdraw fluids.

The term "needle-penetrable sealing septum" means a barrier which is penetrable by a medical needle, which forms a seal around the needle during sealing and provides a seal against any substantial fluid flow after withdraw of the needle.

The term "operator force" means force applied by a human, most typically a doctor, nurse, or medical technician using their hand, thumb, finger or tool(s), or combinations thereof.

The term "outward" means the opposite of inward.

The term "patient" means a medical patient, human or animal.

The term "radio imaging" means creating an image or visualization using electromagnetic spectrum wave technology, including without limitation, fluoroscopy, x-rays, or otherwise.

The term "radio-opaque indicia" is one or more letters, numbers, symbols and/or marking which sufficiently stops or impedes waves from radio imaging such as to be visible via radio imaging.

The term "subcutaneous" means under the skin of a patient.

The term "track" means one or more structures forming a path for movement. The track may be linear, curvilinear, serpentine, complex, or otherwise. The track may be in the nature of a rail, projection, tab, dove tail, wheel, or otherwise, and also may be in the nature of a groove, trough, conduit or otherwise, alone or in combination with each other.

The term "unlocked position" means a spatial relationship wherein a lock does not hold a given item in place.

The term "urge" means to move using force.

The term "yoke" means a structure having at least two projections, members or arms (or a combination thereof) extendible on either side of something.

Articles and phases such as, "the", "a", "an", "at least one", and "a first", are not limited to mean only one, but rather are inclusive and open ended to also include, optionally, two or more of such elements.

The language used in the claims and the written description is to only have its plain and ordinary meaning, except as explicitly defined above. Such plain and ordinary meaning is inclusive of all consistent dictionary definitions from the most recently published (on the filing date of this application) general purpose Webster's dictionaries and Random House dictionaries.

Referring to the drawing figures, an access port 100 for subcutaneous use in a patient is disclosed. Preferably, includes a housing 80 with a chamber 81 in the housing. The port also includes a needle-penetrable sealing septum 82 (having top surface 83; see FIGS. 5A and B) providing needle access to chamber 81. For example, such access typically consists of a needle penetrating beyond top surface 83 of the septum 82 and into chamber 81. The septum typically provides a fluid tight seal around the needle while inserted, and re-closes to substantially seal off after the needle is withdrawn. Normally, in use, the port 100, being subcutaneous, contemplates the needle being penetrated through the skin (percutaneously) and then through the septum 82. Optionally (not shown) the port may have one or more tactile bumps, ribs, or other features that may be discerned by an operator through the patient's skin for identification or other purposes.

The port also preferably includes a projection, typically a male projection 84 having a conduit 85 to chamber 81. The projection is adapted to receive a catheter C thereover.

The access port also includes a lock, such as for example lock 40. Preferably, the lock is attached to the port and is movable with respect to the housing.

For example, FIG. 1A shows catheter C in isolation from port 100. Catheter C is moved in axial direction A, as shown in FIG. 1, axially over projection 84, such as shown in FIG. 1B.

Figure 1B:
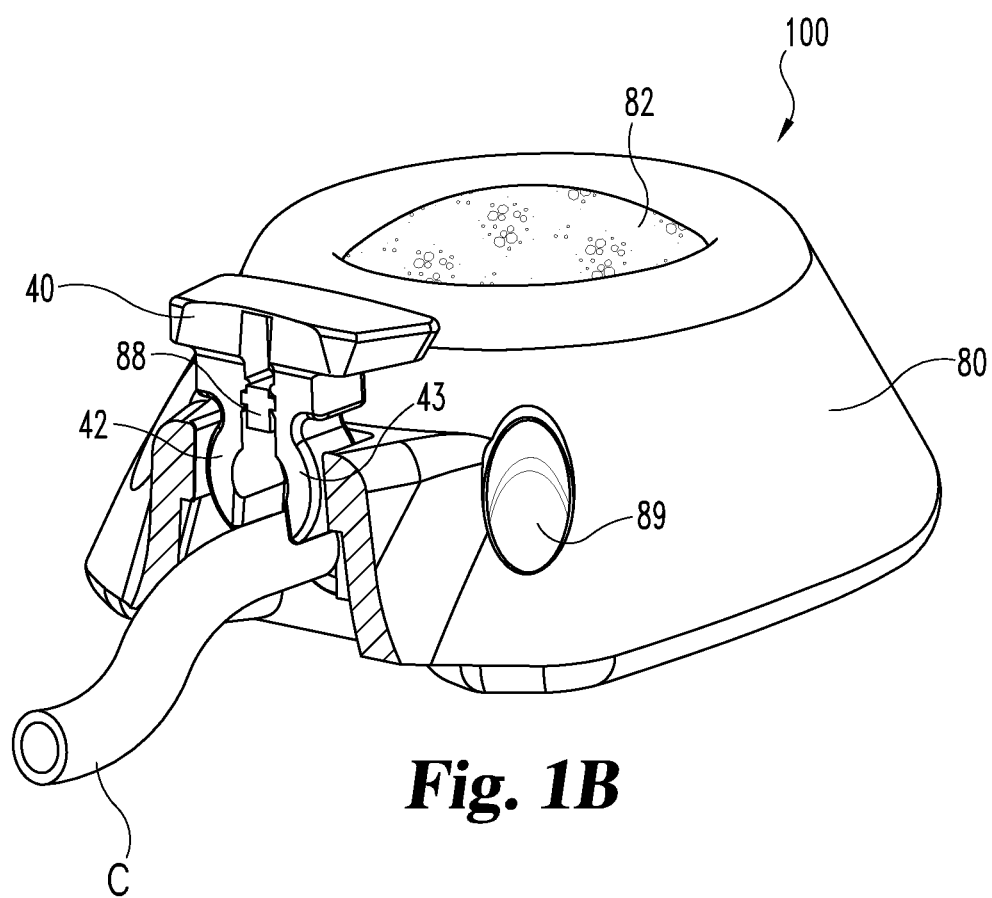
FIG. 1B is the device of FIG. 1A with a catheter received thereon and with a lock in an unlocked position.
Figure 1C:
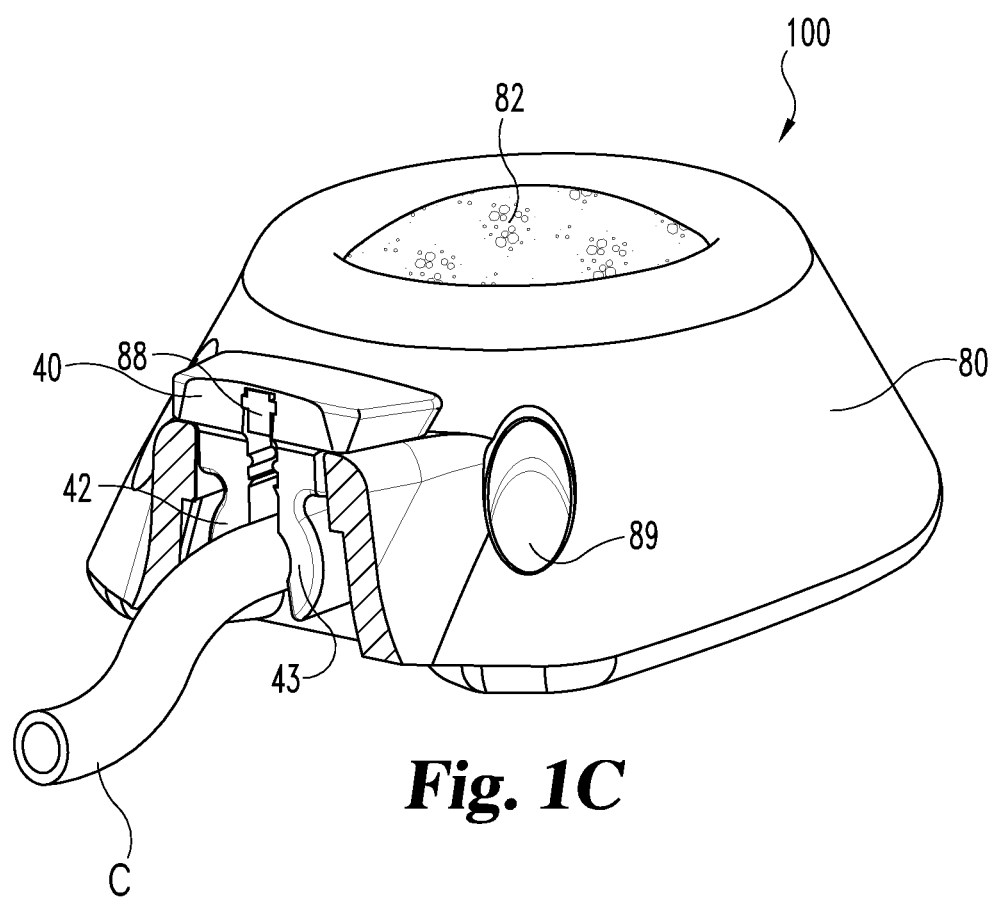
FIG. 1C shows the device of FIG. 1B in a locked position.
Figure 2A:
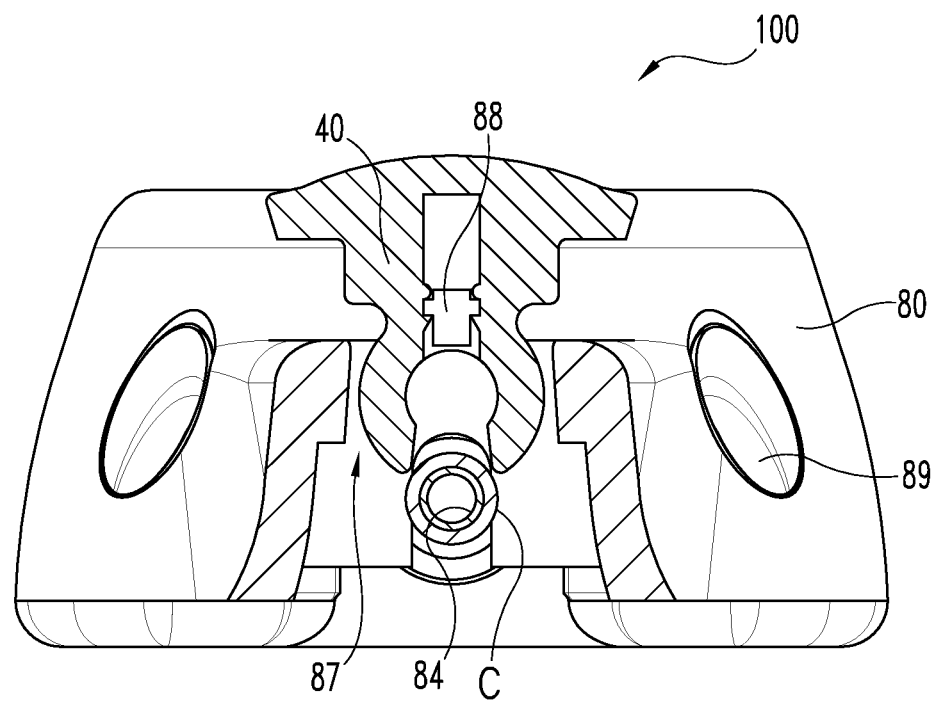
FIG. 2A is a frontal, partial section view of a device of FIG. 1B.
Figure 2B:
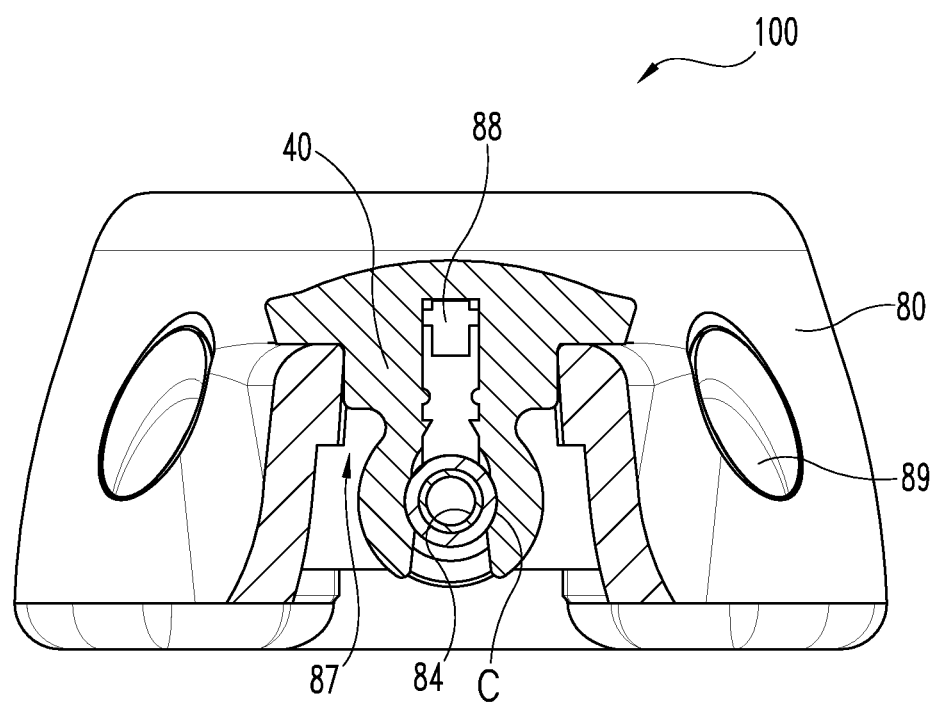
FIG. 2B is a frontal, partial section view of a device of FIG. 1C.

The lock may have two or more positions, including an unlocked position (as illustrated in FIGS. 1B and 2B). It is movable in a direction generally traverse to male projection 84 to a locked position (as shown in FIGS. 1C and 2C). This forces at least a first member 42 of the lock inward toward the catheter C to apply inward force to help hold the catheter onto projection 84. Optionally, the lock is attached to the remainder of port 100.

Optionally, lock 40 and its first member are integral, and the first member is adapted to elastically to form outward around the catheter during the generally transverse movement of the lock into the after move inward toward the catheter to apply force thereto. However, they optionally may be non-integral.

Optionally, port 100 includes at least one track 88 and 46 and/or 87, optionally the lock is movable along such track from an unlocked position to a locked position (see FIGS. 1B-3A and 4-5B).

The lock can take any shape or configuration. Optionally, it may include a yoke such as illustrated in FIG. 3 or otherwise. The yoke may optionally include a first member 42 and an interval second member 43 generally opposite to member 42 and adapted to apply inward force, toward member 42, to hold a catheter onto a projection. The operator force T (see FIG. 1A) may urge the lock towards and into the locked position.

Optionally, the port may include one or more detents. Such detents may hold a lock in an unlocked position or in a locked position, or both. Likewise, the present invention can optionally include no such detent. The detents may be in, along to, or next to a track as aforementioned. However, such detents may be elsewhere between or near the lock and the housing and/or port. For example, as illustrated in FIG. 3, several optional detents 47a, 47b, 47c and 47d are disclosed. Detents may take any shape, but for example, detents 47b and 47d are effectively barbed in that they have a sharp edge with an abutment surface and an opposed slanting or cam surface. Such arrangement facilitates movement in one direction while blocking, or at least substantially resisting movement in the opposite direction. For example, detents 47b and 47d may be used in assembly of the port with lock 40, such that once assemble lock 40 will remain unitary with the housing 80 and not drop separately into the surgical site or on the operating room floor. Another example of a detent shaped option is 47a and 47c which do not have such barbing feature, but rather are more symmetric. As illustrated, they have rounded surfaces, such as a curved, cylindrical, or as illustrated a hemi-cylindrical shape. More or less detents may be used. In this particular example, which is not limiting, as shown in the drawings, such detents may interface with member 88. In particular, with reference to FIGS. 2A and 4, member 88 has one or more protrusions, such as protrusions 90a and 90b. Such protrusions engage and/or interact with the previously described detents. For example, as shown in FIG. 2B, such projections are positioned in between the respective detents 47a/47c and the other detents 47b and 47d, holding the lock in an open position. By applying downward force T as shown by the arrow in FIG. 1A, the detents are moved apart. Optionally, when the device is in a locked position such detents may engage member 88, or any other member, and assist holding the lock in a locked position. Note also that members 42 and 43 are in a closed position (see FIG. 1C), the members wrapping around the catheter also hold it in a locked position.

Figure 3A:
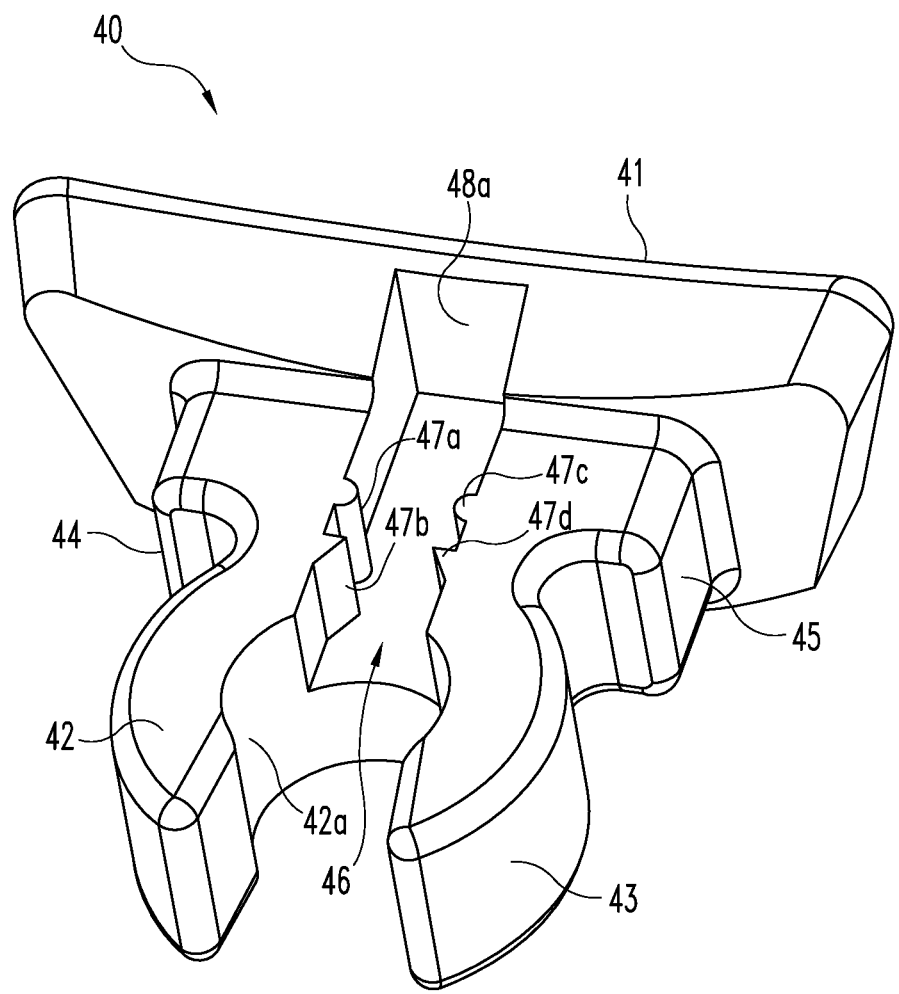
FIG. 3A is a perspective view of one example of a lock usable in the present invention shown in isolation.
Figure 3B:
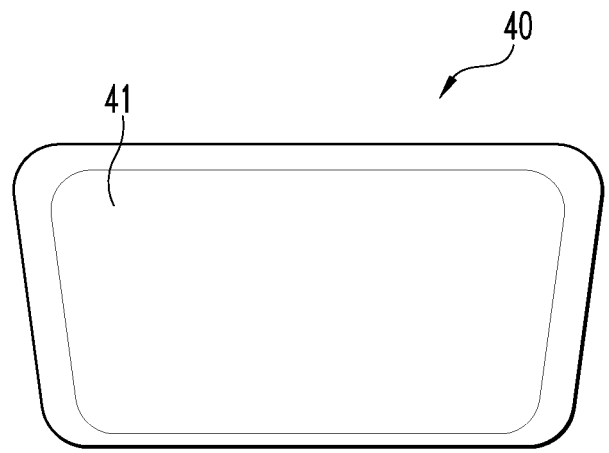
FIG. 3B is a top plan view of the lock of FIG. 3A.
Figure 3C:
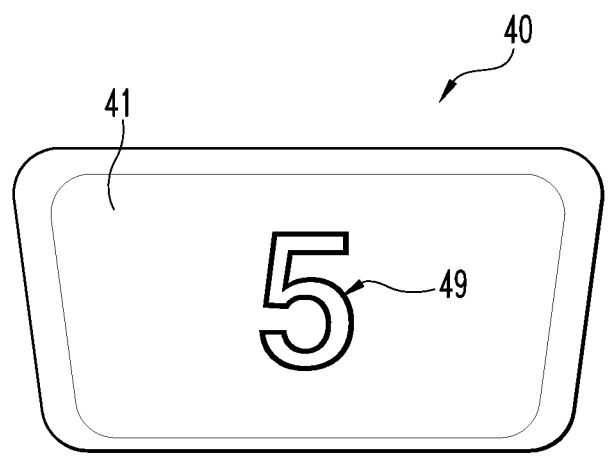
FIG. 3C is a top plan view of an alternative version of the lock of FIG. 3A.
Figure 4:
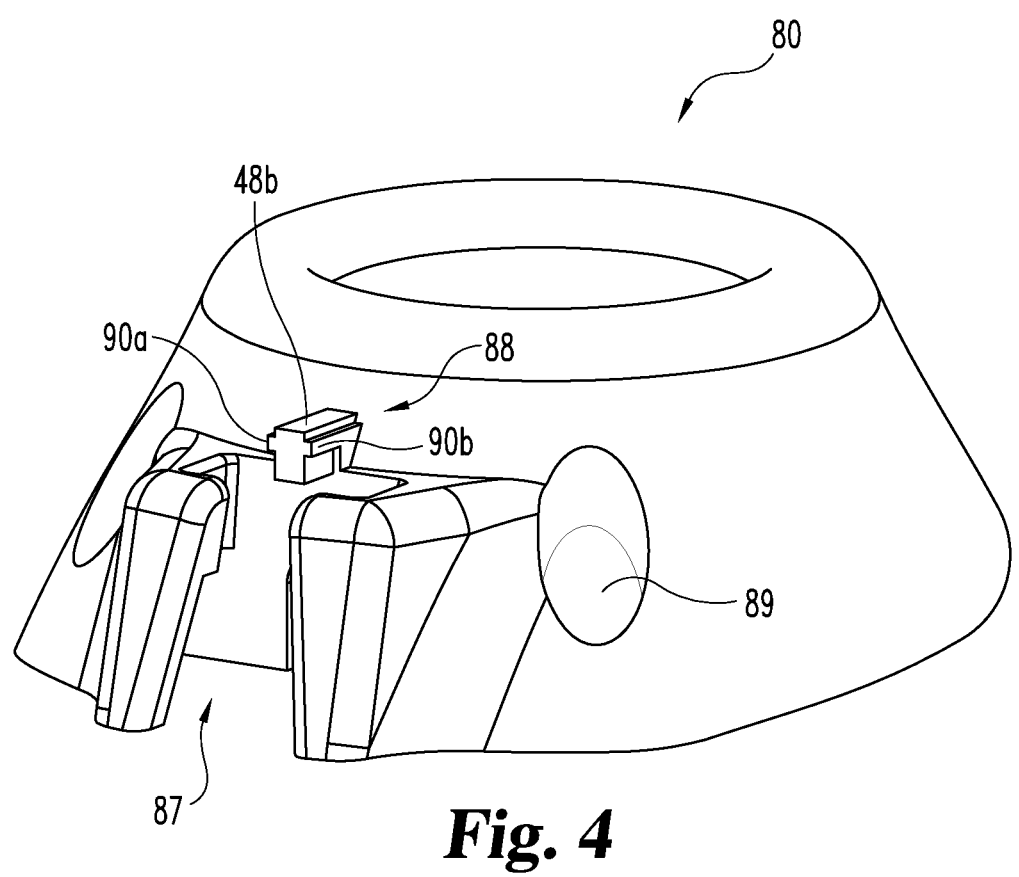
FIG. 4 is a perspective view of one example of a housing usable in the present invention shown in isolation.

Optionally, lock 40 may include indicia 49 thereon (see FIG. 3C). Such indicia may include, but is not limited to, radio-opaque indicia identifying port attributes in radio imaging. In the illustrated example, the number "5" may be used to signify milliliter flow rate rating for the port, or otherwise. Letters such as "CT", or trademarks, or otherwise may be used. Likewise, such indicia may optionally be excluded from lock 40, as shown in FIG. 3B. Also, optionally indicia may be located elsewhere on the port, such as on the bottom 80c and/or surface 83, or otherwise, or not at all.

In those illustrated examples, the lock 40 is arranged to require force downward to move the lock from an unlocked position to a locked position. This can include detents, as previously described, friction fit, frangible member(s), movement of blocking member(s), cam action, shearing, or otherwise.

Optionally, the movable feature as between the lock on the one hand and the port and/or port housing on the other hand, may be accomplished in a variety of ways. As previously described, this may include movement along a track, such as a straight or linear track. However, any other movement is allowed. For example, it may be movement along a curvilinear track. Also, optionally, it could be movement around one or more pivots, with such pivots having pivot axis, horizontal, vertical, diagonal or otherwise. Preferably, such pivot axis will be generally skew to the axis of projection 84, such as for example perpendicular but offset from such projection. This allows a pivoting lock to move generally transverse to the catheter, swinging the lock into engagement around the catheter in a generally transverse, albeit curved arc of movement. Optionally, such movement may also be provided by gear movement, whether conventional gear, bevel gear, and/or gear rack. Moreover, such movement may be compound movement, such as a combination of movement along a combination of slides, tracks, pivots, gears and/or otherwise.

Also, such force in part to the lock may be direct or indirect. For example, it may be forced transferred by one or more intervening member or members. One such way of imparting motion is through a lever or cam action. Such optional approach allows flexibility of design, providing for a lower profile and/or a change of the orientation of operator force vis-à-vis the orientation of transverse movement to urge a lock in to the locked position. It may also provide a mechanical advantage such as leverage or otherwise in urging the lock to the locked position.

Optionally, housing 80 may include one or more apertures, such as aperture 89, or other fittings to allow suturing or other fastening of the port in place. Lock 40 may be provided in any one of hundreds of configurations. It may be a single piece or multiple pieces. The example in FIG. 3A is only that, an example. It has a generally T-shaped configuration with top surface 41 providing an enlarged surface for operator finger or thumb contact. As mentioned, it may include a yoke structure as well, such as formed by members 42 and 43. As illustrated, interior surface 42a contacts a catheter. Slot or groove or track, such as 46 may be provided on the inside, outside, or otherwise, with or without detents. In this specific example, an abutment surface 48a may be provided anywhere, and in this case is provided on the inside top of such slot. Optionally, abutment surface 48a may abut the corresponding top abutment surface of 48b (see FIG. 4) of projection 88. Lock 40 may also have side or otherwise elements that are projection or provider profile such as members 44 and 45. These may provide elements to slide in a track, such as illustrated that they are sliding in track 88.

Figure 5A:
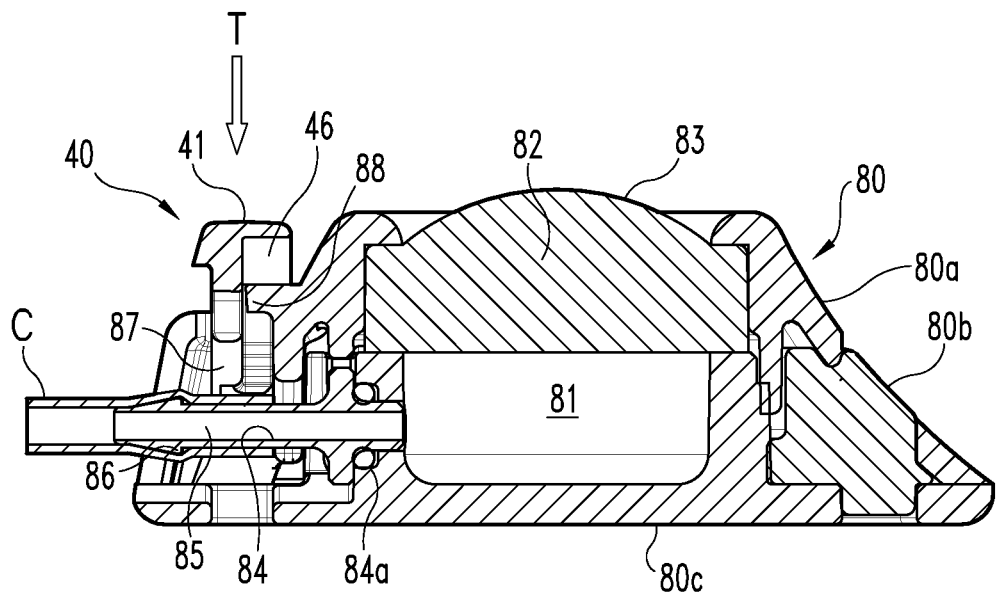
FIG. 5A is a side cross-sectional view of the device of FIG. 1B, showing the device in an unlocked position.
Figure 5B:
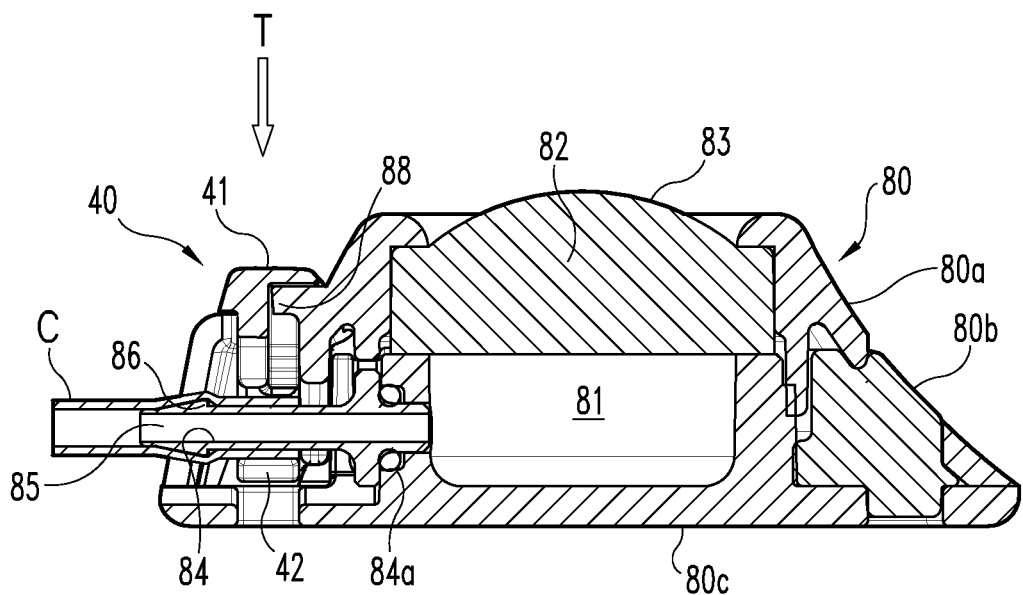
FIG. 5B is a side cross-sectional view of the device of FIG. 1C, showing the device in an locked position.

Note that the example port shown in the drawings is shown in cross-section in FIG. 5A (unlocked position) and FIG. 5B (locked position). Housing 80 may be made of any type of material (metal, plastic, and/or otherwise) and may be made of one, two or more pieces, such as including various housing portions, such as upper housing portion 80a, intermediate housing portion 80b and housing base portion 80c. In this particular example, the base portion 80c may wholly or partially define the bottom surface of the port.

Projection 84 may optionally include a barb portion 86 (see FIGS. 5A and 5B) which may form a barb action for engagement with catheter C to provide further resistance against withdraw of the catheter. Optionally, no barb or flared portion may be provided, or multiple the projection may have barb (b) located inboard and/or outboard or both of lock member 40. Projection 84 includes one or more conduits, such as conduit 85 (see FIGS. 5A and 5B) through it. The projection may be integrally molded, but typically is separately formed from the reminder of housing 80. Optionally, sealing, such as by fusing, glue and/or o-rings (see for example, o-ring 84a in FIGS. 5A and 5B) may be provided to help maintain a fluid tight seal.

Figure 6:
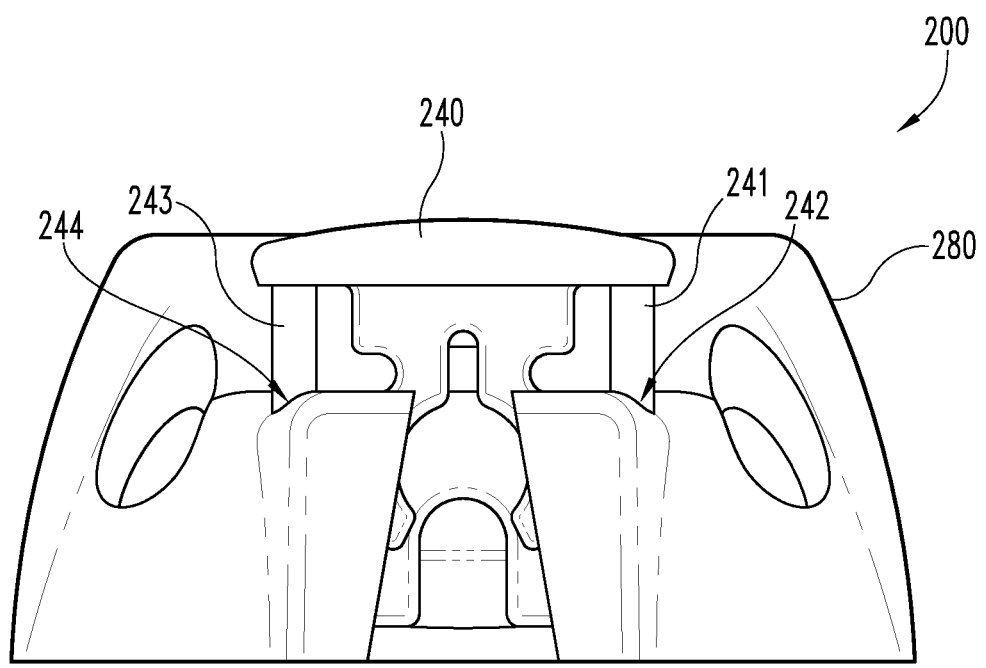
FIG. 6 is front view of an alternative example of a device according to the present invention, showing the device in an unlocked position.
Figure 7:
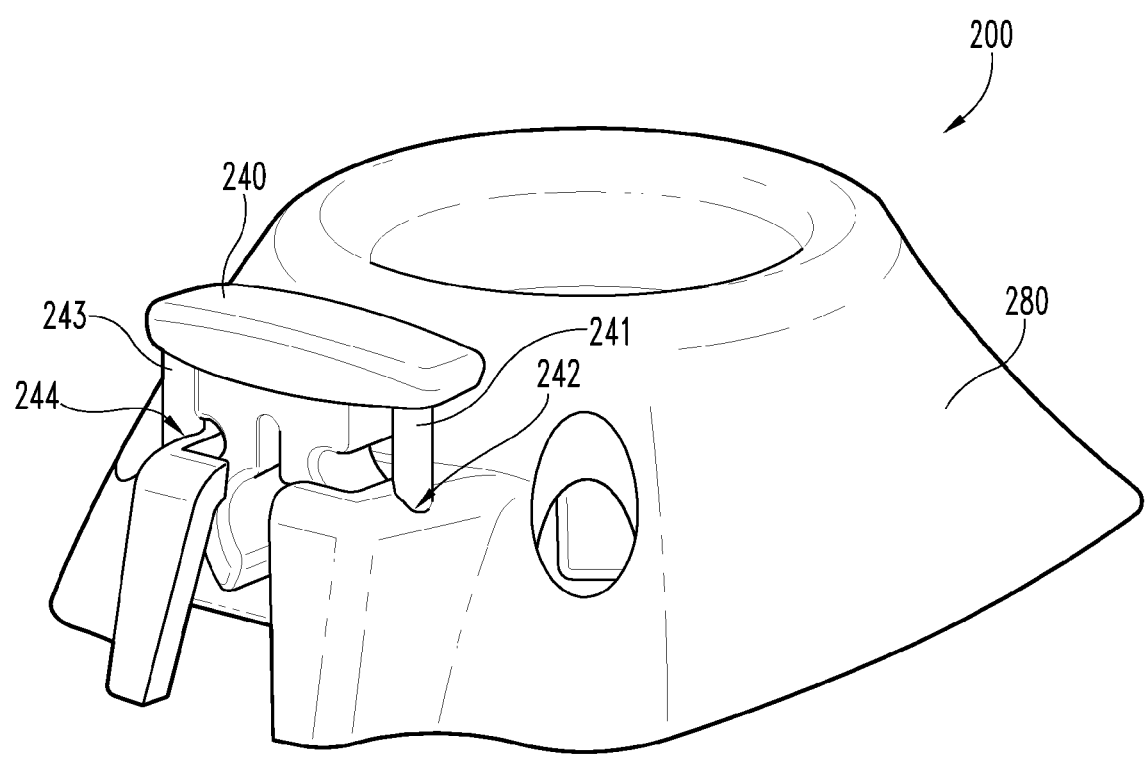
FIG. 7 is a perspective view of the device of FIG. 6.

FIGS. 6 and 7 show an alternative arrangement 200 having housing 280 and lock 240. However, additional tracks are provided in connection with lock 240. Specifically, by way of non-limiting example, tracks 241, 242, 243 and 244 are shown. In this example, such tracks are a pair of parallel pins, such as pin 241 and pin 243. The pin(s) may slide or otherwise travel in the respective apertures 242 and 243 from the open position (as shown in FIGS. 6 and 7) to a closed position. One or more of such pins and apertures may be inverted or reversed. For example, instead one may optionally provide pins (or other such tracks) on the housing, with apertures (or other such tracks) in the lock. As shown, the pins are straight, but could be curved or otherwise. In this particular example, the pins are molded and integral with lock 240. The pins are shown in this example as being outboard of the other tracks, but may be otherwise, and/or may be used in lieu of other tracks.

While the invention has been illustrated and described in detail in the drawings and foregoing description, the same is to be considered as illustrative and not restrictive in character, it being understood that only the preferred embodiment has been shown and described and that all changes, equivalents, and modifications that come within the spirit of the inventions defined by following claims are desired to be protected. All publications, patents, and patent applications cited in this specification are herein incorporated by reference as if each individual publication, patent, or patent application were specifically and individually indicated to be incorporated by reference and set forth in its entirety herein.

The invention claimed is:

1. An access port for subcutaneous use in a patient, comprising:
   a housing;
   a chamber in said housing;
   a needle-penetrable sealing septum providing needle access to said chamber;
   a male projection having therein a conduit to said chamber, said projection adapted to receive a catheter thereover;

a lock, said lock attached to the port and movable with respect to said housing;

a track in said housing, said track being generally transverse to and at a location along a length of said male projection;

wherein said lock from an unlocked position is movable along said track in said housing in a direction generally transverse to said male projection to a locked position forcing at least a first member around said male projection and around the catheter and inward toward the catheter to apply inward force around said male projection and around the catheter to apply inward force to the catheter to help hold a catheter onto said projection.

2. The port of claim 1, wherein said lock and said first member are integral, and wherein said first member is adapted to elastically deform outward around the catheter during said generally transverse movement of said lock and to thereafter move inward toward the catheter to apply force thereto.

3. The port of claim 2, wherein said lock includes a yoke, said yoke including said first member and an integral second member generally opposite to said first member and adapted to apply inward force, toward said first member, to help hold a catheter onto said projection.

4. The port of claim 3, wherein said lock is held by a detent in said unlocked position until overcome by operator force to urge the lock toward said locked position.

5. The port of claim 4, wherein said lock includes a button comprising an enlarged surface for operator finger or thumb contact, wherein said button includes alphanumeric radio-opaque indicia thereon to identify port attributes in radio imaging.

6. The port of claim 5, wherein said lock is arranged to require force downward to move said lock from said unlocked to said locked position.

7. The port of claim 1, wherein said lock includes a yoke, said yoke including said first member and an integral second member generally opposite to said first member and adapted to apply inward force, toward said first member, to help hold a catheter onto said projection.

8. The port of claim 7, wherein said lock is held by a detent in said unlocked position until overcome by operator force to urge the lock toward said locked position.

9. The port of claim 7, wherein said lock includes alphanumeric radio-opaque indicia thereon to identify port attributes in radio imaging.

10. The port of claim 1, wherein said lock is held by a detent in said unlocked position until overcome by operator force to urge the lock toward said locked position.

11. The port of claim 1 wherein said lock includes a button comprising an enlarged surface for operator finger or thumb contact, wherein said button includes alphanumeric radio-opaque indicia thereon to identify port attributes in radio imaging.

12. The port of claim 1, wherein said lock is arranged to require force downward to move said lock from said unlocked to said locked position.

13. An access port for subcutaneous use in a patient, comprising:

a housing;

a chamber in said housing;

a needle-penetrable sealing septum providing needle access to said chamber;

a male projection having therein a conduit to said chamber, said projection adapted to receive a catheter thereover;

a locking button comprising an enlarged surface for operator finger or thumb contact, wherein said locking button is arranged to require force downward to move said locking button from an unlocked to a locked position; and, wherein said locking button includes a yoke, said yoke including an integral first member and an integral second member generally opposite to said first member and at a location along a length of said projection and adapted to apply inward force on the catheter and toward each other to help hold a catheter onto said projection; and, wherein said locking button includes alphanumeric radio-opaque indicia thereon to identify port attributes in radio imaging.

14. The port of claim 13, wherein the port includes at least one track, and wherein said locking button is movable along said track from said unlocked position to said locked position.

15. The port of claim 14, wherein said first member and said second member are adapted to elastically deform outward around the catheter during generally transverse movement of said locking button and to thereafter move inward toward the catheter to apply force thereto.

16. The port of claim 15, wherein said locking button is held by a detent in said unlocked position until overcome by operator force to urge the locking button toward said locked position.

17. The port of claim 13, wherein said first member and said second member are adapted to elastically deform outward around the catheter during generally transverse movement of said locking button and to thereafter move inward toward the catheter to apply force thereto.

18. The port of claim 13, wherein said locking button is held by a detent in said unlocked position until overcome by operator force to urge the locking button toward said locked position.

* * * * *

UNITED STATES PATENT AND TRADEMARK OFFICE
CERTIFICATE OF CORRECTION

PATENT NO. : 8,657,795 B2
APPLICATION NO. : 12/649696
DATED : February 25, 2014
INVENTOR(S) : Christopher N. Magalich It is certified that error appears in the above-identified patent and that said Letters Patent is hereby corrected as shown below:

In the Specification

In column 4, line 28, replace "Optionally, port 100 includes at least one track 88 and 46 and/or 87," with --Optionally, port 100 includes at least one track 88 and 46 and/or 44 and 88,--

Signed and Sealed this
Fifteenth Day of July, 2014

Michelle K. Lee
*Deputy Director of the United States Patent and Trademark Office*